United States Patent
Bunce et al.

[11] Patent Number: 5,916,521
[45] Date of Patent: Jun. 29, 1999

[54] LATERAL FLOW FILTER DEVICES FOR SEPARATION OF BODY FLUIDS FROM PARTICULATE MATERIALS

[75] Inventors: Roger Abraham Bunce; Gary Harold Gregory Henry Thorpe; Jan Christina Hall, all of Birmingham, United Kingdom; Philip Poissant, Toronto, Canada

[73] Assignee: Spectral Diagnostics, Inc., Ontario, Canada

[21] Appl. No.: 08/878,733

[22] Filed: Jun. 19, 1997

Related U.S. Application Data

[63] Continuation of application No. 08/368,790, Jan. 4, 1995, abandoned.

[51] Int. Cl.⁶ ................................................. G01N 33/48
[52] U.S. Cl. .............................. 422/56; 422/61; 422/58; 422/101
[58] Field of Search ................... 422/56, 58, 61, 422/101

[56] References Cited

U.S. PATENT DOCUMENTS

| | | |
|---|---|---|
| 4,631,050 | 12/1986 | Reed et al. . |
| 4,770,777 | 9/1988 | Steadly et al. . |
| 4,839,296 | 6/1989 | Kennedy et al. . |
| 4,904,385 | 2/1990 | Wessling et al. . |
| 4,933,081 | 6/1990 | Sasaki et al. . |
| 5,017,292 | 5/1991 | DiLeo et al. . |
| 5,139,685 | 8/1992 | de Castro et al. . |
| 5,147,606 | 9/1992 | Charlton et al. ............... 422/58 |
| 5,152,743 | 10/1992 | Gorsuch et al. . |
| 5,190,657 | 3/1993 | Heagle et al. . |
| 5,240,862 | 8/1993 | Koenhen et al. . |
| 5,262,067 | 11/1993 | Wilk et al. . |
| 5,298,165 | 3/1994 | Oka et al. . |
| B1 4,477,575 | 4/1992 | Vogel et al. . |

FOREIGN PATENT DOCUMENTS

| | | |
|---|---|---|
| 1177374 | 11/1984 | Canada . |
| 2023738 | 2/1991 | Canada . |
| 2019424 | 8/1991 | Canada . |
| 1307448 | 9/1992 | Canada . |
| 1313130 | 1/1993 | Canada . |
| 1314795 | 3/1993 | Canada . |
| 2118686 | 3/1993 | Canada . |
| 1322335 | 9/1993 | Canada . |

*Primary Examiner*—Lyle A. Alexander
*Attorney, Agent, or Firm*—Klauber & Jackson

[57] ABSTRACT

The invention relates to a filter device for use in diagnostic assay procedures for the effective separation of unwanted particulate matter from the liquid sample of an analyte. The device comprises plural sheet-like cappillary forms prepared from porous media, and that are able to receive and filter the liquid sample. The filter is so configured that, as the pores of the porous media become blocked, the liquid and any particulate matter contained therein are able to travel laterally, and then transversly, to unblocked regions of pores, thereby facilitating optimal speed and efficiency of sample processing. The invention extends to test kits for medical technologists that embody the filter device, and to corresponding methods of testing comprising the separation of particulate matter from samples such as body fluids and the like.

39 Claims, 7 Drawing Sheets

LATERAL FLOW FILTER DEVICES FOR SEPARATION OF BODY FLUIDS FROM PARTICULATE MATERIALS

This application is a continuation of application Ser. No. 08/368,790, filed Jan. 4, 1995 now abandoned.

FIELD OF THE INVENTION

This invention relates to devices and process for the filtering and separation of a body fluid from particulate materials in said fluid, to be used primarily but not exclusively, in chemical analysis of biological materials and testing kits for said separation and analysis.

BACKGROUND OF THE INVENTION

An analyte of interest is often contained in the liquid phase of the material such as body fluid, to be analyzed. Particulate matter present in body fluids, needs to be removed prior to analysis, because material such as thrombocytes, erythrocytes and leukocytes in whole blood, may interfere with the usual analytical chemical techniques used in the determination of the presence and concentration of certain dissolved components, leading to an inaccurate result. For example, in the case of human blood analysis, most analytical tests need to be performed on the serum or plasma, and this first requires removal of the erythrocyte, which would otherwise interfere optically and/or chemically with the test.

Such problems resulting from the interference of particulate materials with the analytical technique and the methods utilized to remove the particulate material from the fluid being analyzed have been reviewed in Canadian Patent No. 1,322,335 as well as Canadian Patent No. 1,177,374. Traditionally, serum or plasma is separated from the erythrocytes by centrifugation, a process which involves expensive equipment and the use of reagents which may be hazardous to humans. In addition, this method requires relatively large quantities of blood, is manually intensive and is generally regarded as only suitable for use in laboratories by properly trained staff.

As such, there has been a growing interest in rapid, simple to use, disposable diagnostic devices which require only slight amounts of blood or body fluid, do not require laboratory facilities, and which can be used by non-chemists. These devices generally involve flow of the body fluid through a filtering medium and the use of lyophilized reagents (U.S. Pat No. 5,198,193, Bunce et al.). The more traditional centrifugation method for collecting fluids such as plasma free of particulates is incompatible with this type of technique.

The use of filtering methods compatible with porous media devices to provide for simple, inexpensive separation of small volumes of plasma has been disclosed in Canadian Patent No. 1,177,374 (Vogel et al., Boehringer Mannheim GmbH) as well as in Canadian Patent No. 1,322,335 (Koenhen et al., Primecare B.V.). Briefly, such devices usually consist of one or more separation layers, on an inert support. The separation layers serve to retain and thus separate the particulate material from the fluid being analyzed, i.e. blood. The fluid then contacts a collection/test layer or layers underneath where reagent(s) which react with the component(s) in the fluid to be determined, cause an observable and measurable change in a physical property (such as by a colour change), and thereby provide a quantitative or semi-quantitative result with respect to the components to be determined.

Canadian Patent No. 1,322,335 teaches use of hydrophilic microporous membranes of a defined pore volume at least one of which is the collector membrane. In a preferred embodiment is taught at least one asymmetric hydrophilic microporous membrane, separator membrane, wherein the body fluid is applied on that side of the asymmetric membrane which contains the largest pores. Thereby, the body fluid with particulate material penetrates immediately into the pores, the particulate material being retained in the pores as they become gradually smaller and the clear fluid penetrating further, to a collection membrane of defined pore volume. The assymetric collector membrane is removed prior to analysis.

One significant aspect of this preferred embodiment is that because of the asymmetric and open pore structure the fluid spreads out in all directions whereas the particulate material does not, whereby it is possible to separate that part of the membrane wherein the particulate materials are retained. This shall be described further herein below.

Filtering devices for use in association with disposable diagnostic devices that will not require laboratory facilities are disclosed in patents or are in commercial use. Canadian Patent No. 1,177,374 teaches a device with glass fibres to separate plasma from whole blood involving a removable glass fibre filter, a collection membrane for a defined volume of plasma and a hydrophobic barrier to prevent erythrocytes from reaching the analytical region. In the filter, there is lateral flow of erythrocytes and plasma. There is also disclosed a hydrophobic mesh to prevent liquid transfer until pressure is applied. There is a gap to prevent premature reaction of the plasma with the analytical reagents.

The Abbott Laboratories TEST PACK* device and Pacific Biotech CARDS* (*Trademarks) represent the use of removable filters for use with urine pregnancy tests and a cup-like holder for securing the filter membrane comprising two molded clamping forms. The holders are arranged to force the membranes into a disc-like form, the underside of which co-acts with the diagnostic membrane. A hydrophobic mesh prevents liquid transfer until the diluent is applied. The filter configuration is circular, and although the area of the filter membrane is larger than both the sample application site, and the area of contact with the analytic means, the additional annular area serves only as a means of retaining the filter.

The Johnson & Johnson LIFE SCAN* glucose strip device also teaches a filter membrane larger than the application site with adhesive to fix the filter membrane position onto the holder. This filter has a uniform pore structure, and it is thought, the large filter area is merely a convenient way of attaching the filter by adhesive.

Some analytes are present in relatively large quantities in blood and can easily be detected in a quantity of blood available from a fingerprick, typically 30µl. Alternatively, some analytical methods are very sensitive, and again only require a small amount of body fluid, i.e. blood. However, the only way some analytes can be detected in meaningful amounts is by using more blood. The amount required may exceed that available from a fingerprick. Furthermore, removal of the erythrocytes using filtration methods becomes more difficult as the filtering capacity of the porous media depends largely on its surface area. If the area is small, the pores quickly become blocked. As the filter area requirement increases, the whole blood application site area and plasma outlet are also increased. Hence, using known constructions, it becomes difficult to apply blood evenly over a large area. It is also difficult to couple the large plasma outlet of the filter to the smaller area of the analytical strip. Furthermore, the whole device can become unacceptably large.

Canadian Patent No. 1,322,335 and the other references do not address the problem associated with known constructions of increasing the volume of plasma available for analysis, and in particular means of interfacing a large filter area to the blood application site, and to the analytical strip.

*Trademark

SUMMARY OF THE INVENTION

Thus, according to the present invention, there is provided a filter device, for use in assay procedures, comprising a filter means having a first sheet-like capillary form connected in laminate manner to a second sheet-like capillary form; said second capillary form comprising porous media having interconnected pores; an inlet region of said first capillary form is arranged to receive liquid containing particulate matter to be filtered, and an outlet region of said second capillary form connects the filtrate therefrom to an assay means; the size of said first capillary form allows coplanar passage of at least part of said particulate matter; said interconnected small pores of second capillary form trap, and prevent passage of particular matter, but allow coplanar passage of said filtrate; said liquid inlet region and said outlet region are arranged so that as said porous media becomes blocked with particulate matter, additional liquid flow, and particulate matter contained therein, travel laterally, and then transversely, to unblocked regions of pores.

In another embodiment of the device according to the invention, the first capillary form comprises porous media having interconnected pores, and which said pores are larger than pores of said second capillary form.

In another embodiment of the device according to the invention, the filter means comprises assymetric porous media having interconnected pores, with a gradation of pore size, from large to small through the thickness of said filter means, from the said inlet region to the said outlet region.

In another embodiment of the device according to the invention, the filter means is folded over on itself in a convoluted superimposed fashion, the end planes being connected to the filtrate and assay means respectively, increasing the absorption capacity of the filter device while allowing connection to the filtration and assay means.

In a further embodiment of the device according to the invention, the sheet filter of the filter device is in a generally cup form, the filter sheet defining the base and at least partial cup walls, the large pore surface generally defining the inner surface and said small pore surface defining the outer surface of said cup walls and base, the inner surface connected at least partially to the filtrate and outer surface base to the assay means; increasing the absorption capacity of the filter device while allowing connection to the filtration and assay means.

According to a second feature, the present invention relates to a process for separating a body fluid from the particulate materials in said fluid, such as plasma from blood, by contacting a slight amount of body fluid with a filter device, for use in assay procedures, comprising a filter means having a first sheet-like capillary form connected in laminate manner to a second sheet-like capillary form; said second capillary form comprising porous media having interconnected pores; an inlet region of said first capillary form is arranged to receive liquid containing particulate matter to be filtered, and an outlet region of said second capillary form connects the filtrate therefrom to an assay means; the size of said first capillary form allows coplanar passage of at least part of said particulate matter; said interconnected small pores of second capillary form trap, and prevent passage of particular matter, but allow coplanar passage of said filtrate; said liquid inlet region and said outlet region are arranged so that as said porous media becomes blocked with particulate matter, additional liquid flow, and particulate matter contained therein, travel laterally, and then transversely, to unblocked regions of pores.

In another embodiment of the process and corresponding device according to the invention, the first capillary form comprises porous media having interconnected pores, and which said pores are larger than pores of said second capillary form.

In another embodiment of the process and corresponding device according to the invention, the filter means comprises assymmetric porous media having interconnected pores, with a gradation of pore size, from large to small through the thickness of said filter means, from the said inlet region to the said outlet region.

In another embodiment of the process and corresponding device according to the invention, the filter means is folded over on itself in a convoluted superimposed fashion, the end planes being connected to the filtrate and assay means respectively, increasing the absorption capacity of the filter device while allowing connection to the filtration and assay means.

In a further embodiment of the process according to the invention, the sheet filter of the filter device is in a generally cup form, the filter sheet defining the base and at least partial cup walls, the large pore surface generally defining the inner surface and said small pore surface defining the outer surface of said cup walls and base, the inner surface connected at least partially to the filtrate and outer surface base to the assay means; increasing the absorption capacity of the filter device while allowing connection to the filtration and assay means.

According to a final feature, the present invention relates to a test kit for the separation and chemical analysis of the components of a body fluid, wherein the complete kit comprises one or more devices according to the present invention.

BRIEF DESCRIPTION OF THE DRAWINGS

The invention is illustrated in particular in preferred embodiments by reference to the accompanying drawings in which:

FIG. 4b is a plan view partly in phantom of the bowed filter device of FIG. 4a;

FIG. 5c is a top perspective view of the filter device of Figure 5a;

DETAILED DESCRIPTION OF THE PREFERRED EMBODIMENTS

FIGS. 1a to 3 are intended mainly to teach the general principles of the invention, but with particular reference to an assay using whole blood.

Figure 1A:
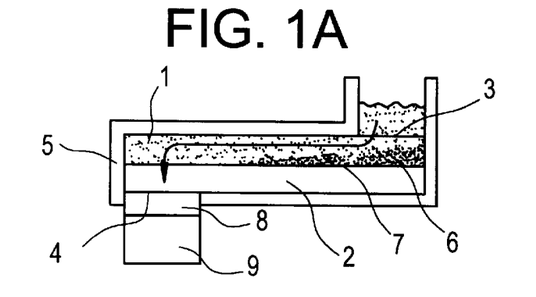
FIG. 1a is a schematic sectional view of a lateral flow filter device in accordance with the invention.

FIG. 1a shows a lateral flow filter device consisting of large pore material 1 in close contact with a smaller pore material 2. The pores of both materials act unidirectionally. The large pore material allows passage of erythrocytes and plasma. The small pore material entraps and prevents passage of erythrocytes, only allowing passage of plasma (providing that the pores have not already been blocked by erythrocytes). The large pore material includes a liquid inlet region 3, and the small pore material is provided with filtrate outlet region 4. Inlet and outlet regions are defined by apertures in housing 5. Small pore material in the region of outlet 4 contacts assay device 9, the form of which depends upon the analyte of interest.

A typical device consists of a plasma collection membrane, a pad containing gold-antibody conjugate, an analytical strip incorporating a region of immobilized antibody to the antigen of interest which may be present in the plasma, and finally a pad to absorb and contain waste liquid (Princeton Biologicals Inc.—Details not shown). In this particular example, outlet 4 is connected, at least initially, to the plasma collection membrane 8 of assay device 9.

In use, a measured volume of whole blood is applied to inlet region 3. Plasma quickly flows into the small pore material 2 in region 6 adjacent to the inlet—because of its higher capillarity. Hence, region 6 begins to clog with erythrocytes. Whole blood continues to be drawn from the inlet region, by the higher capillarity of filter 2 acting on the plasma, and is drawn towards region 7. Plasma flows through this region into filter 2, the surface of which also begins to clog with erythrocytes. The process continues, and a gradation of erythrocytes is formed along the upper surface of filter 2 from inlet to outlet and plasma flows therein. Even if filter 1 and filter 2 are not saturated, and providing the capillarity of collection membrane 8 is higher than that of filter 2, plasma will flow into collection membrane 8.

After a predetermined time, or when all the whole blood has been absorbed, the housing 5, containing the filters 1 and 2 is removed from the assay device. Diluent is added to collection membrane 8 in order to wash plasma contained therein into the gold-antibody conjugate pad where it mixes and reacts (not shown). If the antigen of interest is present in the sample it is labelled with gold conjugate. The reactants wick along the analytical strip, and over the immobilized antibody region. Gold labelled antibody/antigen complex binds to the immobilized antibody to provide a visual indication of the presence, or otherwise, of analyte in the plasma.

Figure 1B:
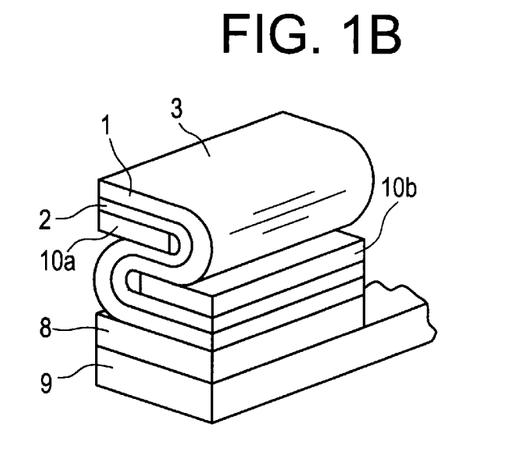
FIG. 1b is a perspective fragmentary view of folded lateral flow filter device.

FIG. 1b shows a folded lateral flow filter device, such that the filter device is folded and is thereby convoluted with superimposed planes. This functions in the same manner as FIG. 1a. The folding merely provides a more convenient format for interfacing the relatively large area of the filter device to the narrow assay strip. Impervious membranes 10a and 10b separate adjacent layers of porous material.

Figure 2:
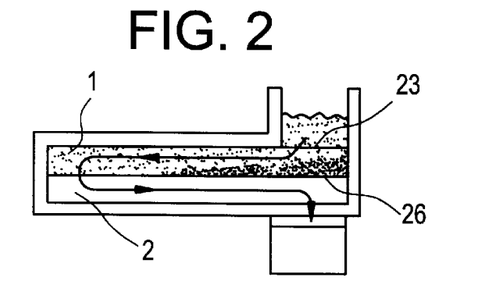
FIG. 2 is a schematic sectional view of a contra-flow filter device.

FIG. 2 shows a contra-flow filter device. This allows the inlet and outlet to the filter device to be placed in-line without the need to fold, and provide impervious separation membranes. The contra-flow filter functions in a similar manner to FIG. 1a. Whole blood is applied to inlet 23. Plasma flows into filter 2, and erythrocytes begin to block filter 2 at region 26. Whole blood flow, within filter 1, begins to be diverted right to left to avoid the partial blockage, and plasma, within filter 2, flows from left to right—hence, contra-flow is established.

Figure 3:
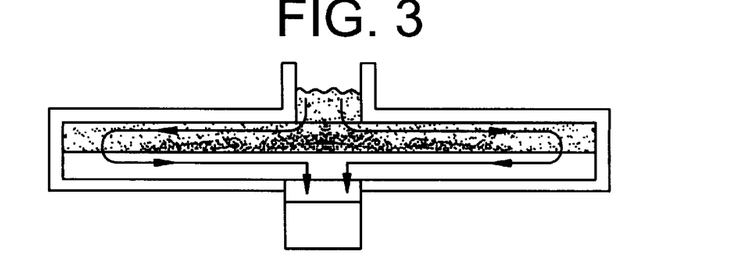
FIG. 3 is a schematic sectional view of a double contra-flow filter device.

FIG. 3 shows a double contra-flow filter device. This symmetrical form is important for product aesthetics, and to provide a more uniform delivery of plasma. Furthermore, combined with the funnel-form of FIG. 5a (to be described), it provides a convenient, high capacity plasma filter, which interfaces readily with existing diagnostic strip devices.

Regarding filter materials: The separate large pore and small pore filters shown in FIGS. 1a–3, and those of other embodiments of the invention, may be replaced by a single asymmetrical membrane filter which has large pores proximal to one surface and small pores proximal to the other. There being a gradation of pore size across the thickness, and the open pore structure allowing coplanar flow within the membrane. Such membranes are produced by Primecare Diagnostics b.v.—a Division of Spectral Diagnostics Inc., Toronto. Use of these so called "Separation" and "Collection" membranes is described in U.S. Pat. No. 5,240,862.

Figure 4A:
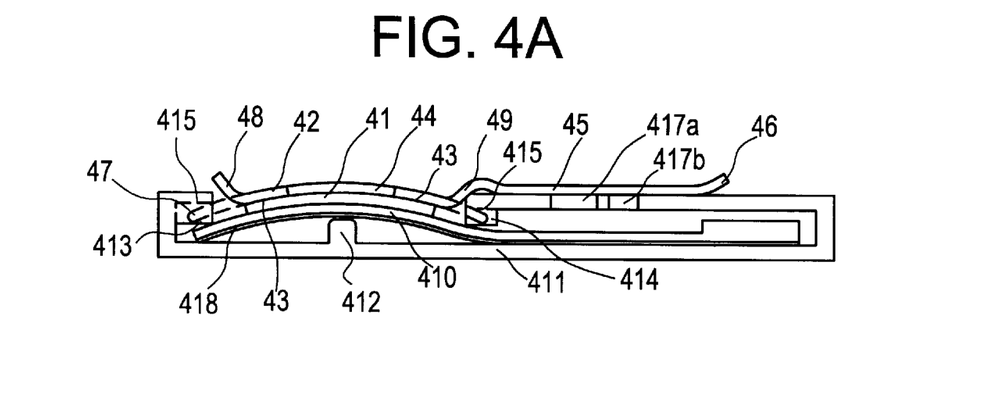
FIG. 4a is a longitudinal section through a "bowed" filter device.
Figure 4B:
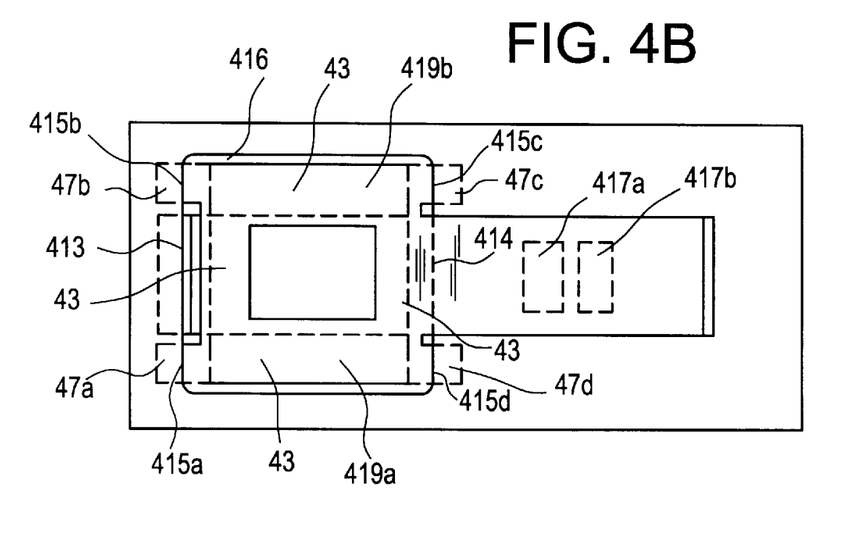
Figure 4C:
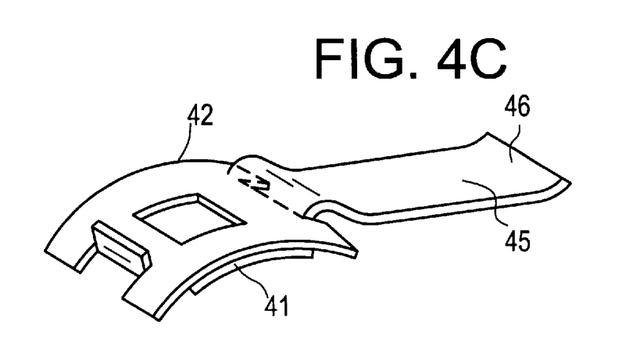
FIG. 4c is a three dimensional view of a bowed filter element.

FIGS. 4a and 4b show a longitudinal section through a "bowed" filter device and a plan view of said device respectively. Primecare Separation Membrane 41 is fixed and sealed to resilient membrane support 42 using 3M Scotch Transfer Adhesive Tape 465 in frame-like manner 43. FIG. 4c shows a three dimensional view of this construction (bowed for clarity). Support 42 is made from an impervious, opaque, plastic material such as Milar (about 0.15 mm thick), and is provided with whole blood inlet aperture 44. Additionally, support 42 incorporates cover region 45, handle 46, four tags 47a–d, and location and rigidity bent forms 48 and 49. Membrane 41 is in close contact with assay strip 410, which may be used to assay for cardiac markers (Spectral Diagnostics Inc.). Housing 411 encloses said assay strip and incorporates abutments 412, 413, 414, and 415*a–d* which coact with said assay strip 410, support 42, and membrane 41 to bend said components into bow-like form. Additionally, housing 411 includes sample application aperture 416, and window apertures 417*a* and 417*b* through which the assay strip and test results thereon can be viewed (after removal of support 42).

Bowing of the test strip ensures close contact between the porous media layers therein, and this provides consistency of liquid flow therethrough. This is because the centre of curvature of test strip is lowered by plastic support layer 418, and abutments 413 and 414 substantially restrain the porous media therebetween. Hence, there is a compression force component acting between constituent porous media layers of the test strip.

Test strip 410 is held in bow-like form independently of membrane support 42 and membrane 41 thereon. In other words, removal of the membrane support does not release compression of the test strip.

There may be several porous media pads in region of the test strip between abutments 413 and 414, and this results in non-uniform curvature of the upper surface. However, since membrane support 42 is made from a resilient material and, in the free state is flat or reverse biased in region 44, uniform contact between membrane 41 and test strip 410 is maintained irrespective of curvature form of the latter. This also self-compensates for variations in manufacturing tolerances.

The composition of the test strip depends upon the assay to be performed. To accommodate most variations of test strip, using this embodiment of the invention, only the height of abutment 412 needs to be modified, thus simplifying and reducing tooling costs.

This method of applying the separation membrane to the test strip, and providing compression thereto, has the advantage that the upper surface of the device is substantially free of obstruction in the sample application region. This is particularly useful in providing an unobscured view of the sample application region when blood is applied directly from a fingerprick.

In use, whole blood is applied to inlet aperture 44. Filter membrane 41 separates and retains the erythrocytes and delivers plasma to assay strip 410. The side regions 419*a* and *b* of membrane 41 serve to increase the filtering capacity. Plasma separation in these regions is via the mechanism of contra-flow and so the device behaves in much the same way as the double contra-flow device of FIG. 3, described previously. Furthermore, the asymmetrical Primecare Separation Membrane behaves similarly to the large pore and small pore membrane therebefore described. Hence, plasma is transferred to the assay strip.

After a predetermined time, or when the whole blood has been absorbed by the top surface of membrane 41, the filter support 42 (and membrane 41 attached thereto) is removed from housing 411 using handle 46. This is easily achieved because membrane support 42 readily flexes causing location tags 47*a–d* to clear aperture 416. During manufacture, fitting of the support 42 is simply the reverse process.

Diluent is then added to the assay strip in region 416, and the assay proceeds as described for FIG. 1*a*. After a predetermined time, the assay result can be read as described previously.

Region 45 of support 42 forms an opaque cover over the test window apertures, and unless the support 42 is removed, the test result cannot be seen. This provides some degree of interlocking against misuse, such as omitting the diluent step. Furthermore, inscriptions on the device could provide interactive operating instructions. Interlocking is described in FIGS. 6*a* and 6*b*, and corresponding text.

This embodiment has a number of useful features but, because of the "flat" form of inlet region 44, sample volume is limited. The next embodiment to be described solves this problem by providing a funnel-form to retain a larger sample volume.

Figure 5A:
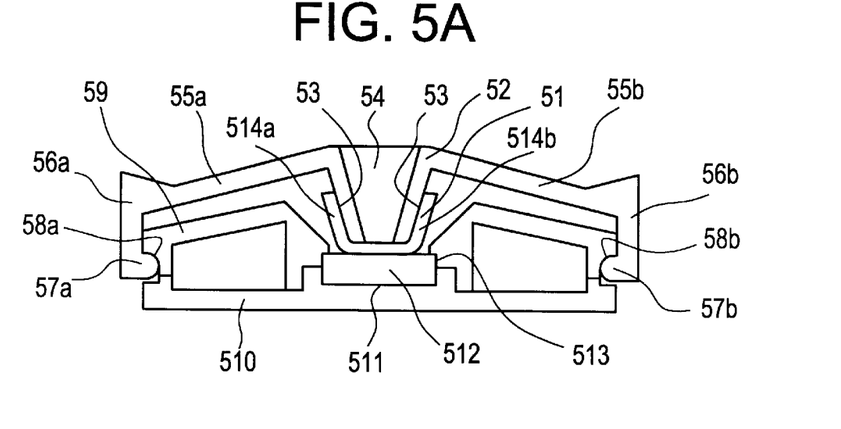
FIG. 5a is a cross-section through a filter device incorporating a "funnel-form"
Figure 5B:
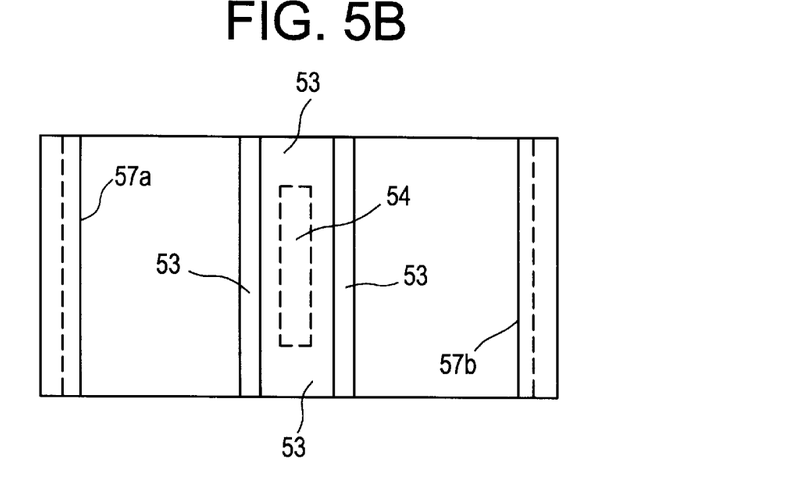
FIG. 5b is a bottom plan view partly in phantom further illustrating the funnel-form filter device.
Figure 5C:
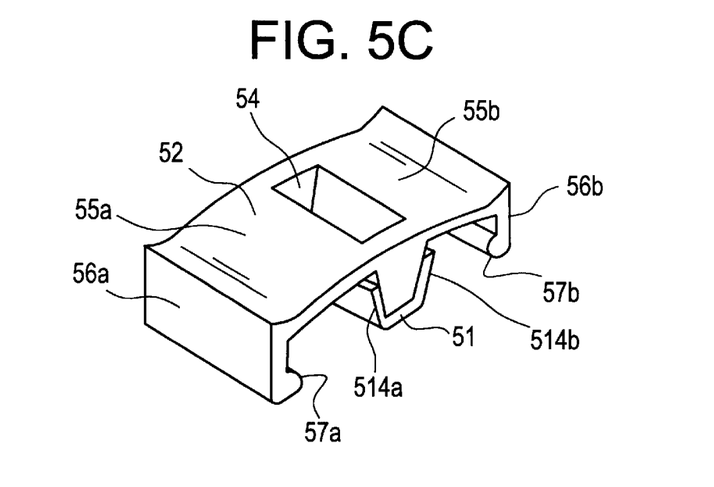

FIGS. 5*a* and *b* show a cross-section and underside view of filter device incorporating funnel-form (hereafter termed funnel) respectively. Primecare Separation Membrane 51 is fixed, and sealed, to funnel 52 using transfer adhesive tape in a frame-like manner 53 around the periphery of membrane 51. FIG. 5*c* shows a three dimensional view of the funnel. Funnel is made from a resilient thermoplastic material, and is provided with whole blood inlet aperture 54. Additionally, funnel 52 incorporates two resilient spring forms 55*a* and *b*, finger grips 56*a* and *b*, and detent latches 57*a* and 57*b*. Latches coact with detents 58*a* and 58*b*, incorporated in upper housing 59. Upper housing is fixed to lower housing 510 using friction dowels (not shown). Lower housing incorporates longitudinal groove 511 which locates assay strip device 512 beneath lower part of membrane 51. Upper housing also incorporates a longitudinal groove 513 which further locates assay strip, and which partly compresses the porous media therein to provide consistency of liquid flow therethrough.

Grooves 511 and 513 hold test strip in position whether or not funnel 52 is present. In other words, removal of funnel does not entirely release compression of the test strip. Spring forms 55*a* and 55*b* serve to bias lower portion of membrane 51 and assay strip 512 together in a controlled manner to ensure consistency of flow therebetween.

Figure 5D:
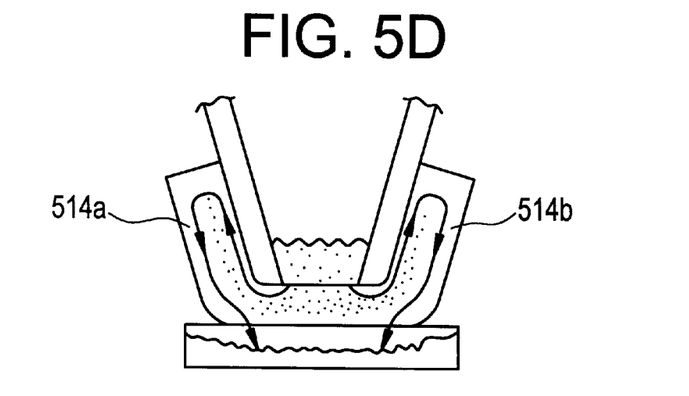
FIG. 5d is a side sectional view illustrating liquid flow in a filter element of the invention.

In use, whole blood is applied to inlet aperture 54. Filter membrane 51 separates and retains the erythrocytes and delivers plasma to assay strip 512. The side regions 514*a* and 514*b* of membrane 51 serve to increase the filtering capacity. Plasma separation in these regions is via the mechanism of contra-flow as shown in FIG. 5*d*. Hence, the device behaves in much the same way as the double contra-flow device of FIG. 3 described previously. Furthermore, the asymmetrical Primecare Separation Membrane behaves similarly to the large pore and small pore membrane therebefore described. Hence, plasma is transferred to the assay strip.

After a predetermined time, or when the whole blood has drained from funnel 52, the funnel (and membrane 51 attached thereto) is removed by lifting upwards from the housing unit using finger grips 56*a* and 56*b*. This causes spring forms 55*a* and 55*b* to deflect releasing said latches and detents. During manufacture, fitting of funnel unit 52 is simply the reverse process.

Diluent is then added to the assay strip in plasma region, and the assay proceeds as described for FIG. 1*a*. After a predetermined time, the assay result can be read as described previously through windows in the housing (not shown).

Figure 5E:
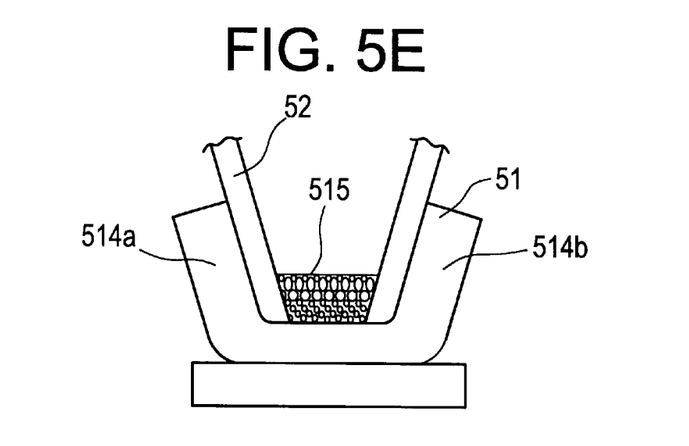
FIG. 5e is a side sectional view of the filter element of FIG. 5d illustrating the prefilter.

The filtering capacity of this, and other herebefore described devices, can be improved by the use of a prefilter as shown in FIG. 5*e*. In this example, prefilter 515 is positioned in funnel 52 adjacent to separation membrane 51. The prefilter is made from glass fibre material and serves to partially remove erythrocytes in order to prevent premature blocking of membrane 51.

Figure 5F:
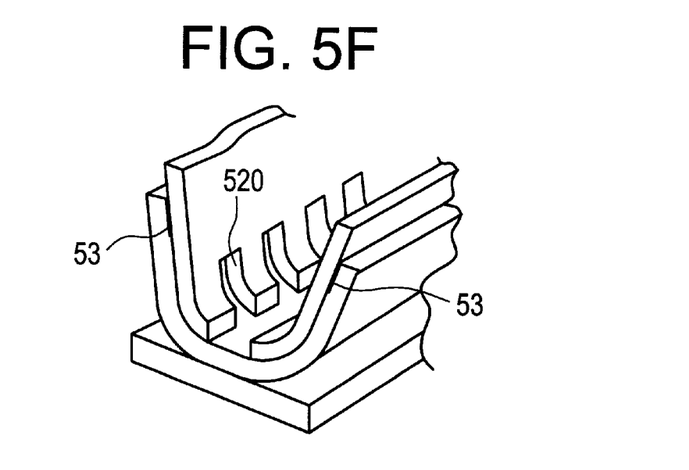
FIG. 5f is a perspective view of a castellated funnel-form in accordance with the invention.

FIG. 5*f* shows a three dimensional cross-sectional view of castellated funnel in which castellations 520 serve to increase the efficiency of the funnel device. This is because the erythrocytes have less distance to travel through the porous media and, for a given volume of whole blood, provides a more even distribution of erythrocytes within the filter. In other words, the possibility of localised blocking of the filter with erythrocytes is reduced.

Figure 5G:
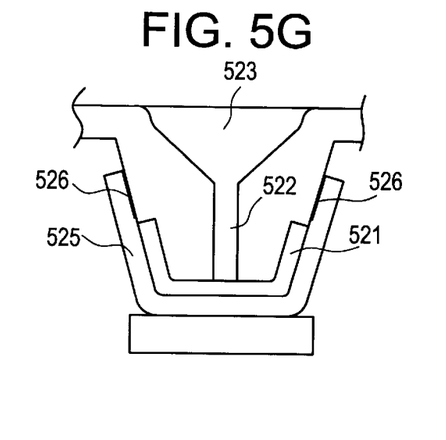
FIG. 5g is a fragmentary side sectional view of a funnel-form incorporating capillary.
Figure 5H:
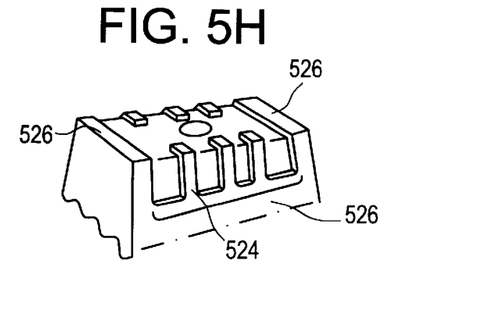
FIG. 5h is a perspective view of the underside of the funnel-form of FIG. 5g.

FIGS. 5g and h show a cross-sectional view and an underside view respectively of a funnel incorporating capillary 521. Channel 522 connects said capillary to blood application cup 523. Castellations 524 coact with membrane 525 to form said capillary 521. The membrane, which may comprise Primecare Separation Membrane, is sealed and fixed into position with frame-like adhesive layer 526. Additionally, capillary 521 may contain porous material to form a prefilter or spreading layer. This serves to trap some erythrocytes, as discussed previously, and also helps to distribute whole blood evenly within capillary.

This device is similar in effect to the castellated form of FIG. 5f. However, comparing FIG. 5g with FIG. 5f, for a given volume of blood, and a given filter area, the surface area of blood directly in contact with the filter is increased. This further promotes even filtration of erythrocytes and minimizes localized blocking. In other words, the funnel is being optimized to provide effective filtration with minimal filter area. Minimizing the filter area reduces lateral flow distances within the porous material and speeds up filtration. Furthermore, excessive area of filter can lead to aesthetic design problems and increased cost of filter membrane.

Effect of haematocrit and sample volume

The filter system must be capable of providing a substantially constant plasma volume to the assay strip with haematocrits ranging from about 30 to 65% and be reasonably immune to variations in blood sample volume. In order to achieve this, a plasma collection membrane (Item 8, FIG. 1) is normally interposed between the separation membrane and test strip and, providing the associated components are designed correctly, this defines plasma volume.

To achieve this, the interrelationship between the characteristics of the various components making up the erythrocyte/plasma separation system needs to be understood. The following hypothesis describes a possible explanation. But firstly some preliminary ideas need to be considered:

1. Filter capacity: The erythrocyte/plasma filtering capacity of the membrane of interest needs to be considered. Obviously, if the area of the membrane is too small the pores will become clogged before the desired volume of plasma has been filtered.

Figure 8A:
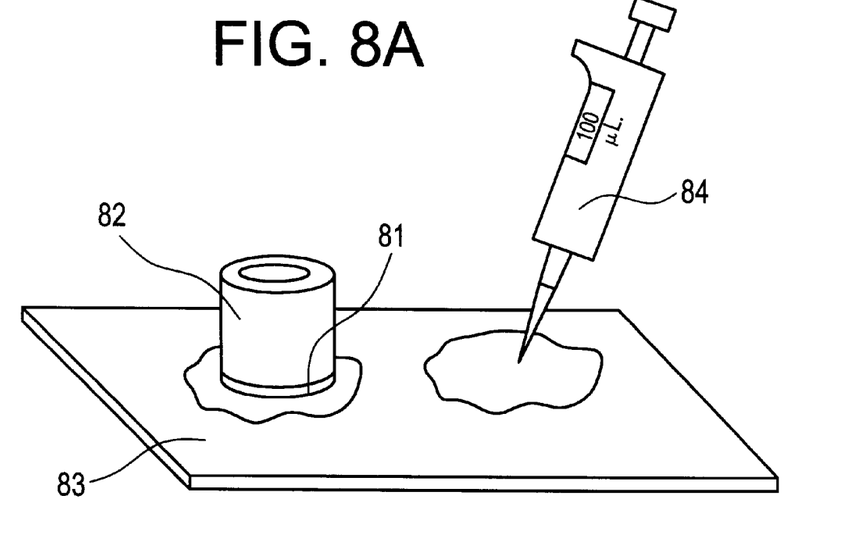
FIG. 8a is a schematic illustration of simple methodology to approximate filter capacity.

Referring to FIG. 8a: A simple method to get an approximate value of filter capacity is to attach a piece of separation membrane 81 onto the lower end of a cylinder 82 and place this on a sheet of collection membrane 83. Blood of known haematocrit is added into the open end of the cylinder, and the diameter of plasma when plasma stops wicking into the collection membrane noted. Provided sufficient blood has been added to the cylinder in the first place, this indicates when the pores of the separation membrane are clogged. To determine the volume of plasma filtered, a sample of the same blood used for the test is centrifuged to separate the plasma, and this is added to the sheet of collection membrane, using a calibrated pipette 84, until the circle of plasma is the same diameter as that produced by the cylindrical device. From this information, the area of separation membrane required to produce a particular volume of plasma from blood of a given haematocrit can be computed.

Figure 8B:
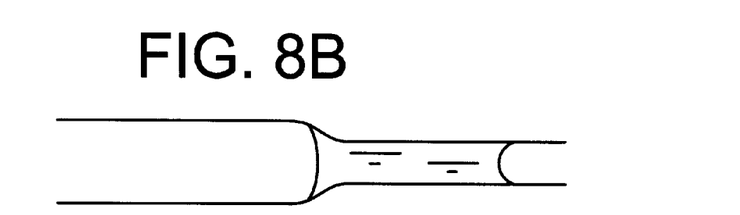
FIG. 8b is a schematic view of a large and small bore capillary tube.

2. Flow between dissimilar sized capillaries: For simplicity, porous material may be considered to behave rather like capillaries. Consider a single capillary comprising a large and small bore tube (FIG. 8b). If liquid is introduced into the junction of the two tubes, liquid flows preferably into the small diameter tube. This may be explained by considering the forces produced by the meniscus. Only when the small diameter is full will liquid begin to flow into the large diameter capillary.

3. Flow in dissimilar porous material: When large pore and small pore material are in contact, and liquid is added slowly to the small pore material, it will not flow into the large pore material until all the small pores are saturated. This assumes that both porous materials have the same surface chemistry, for example, the contact angles are the same.

Figure 8C:
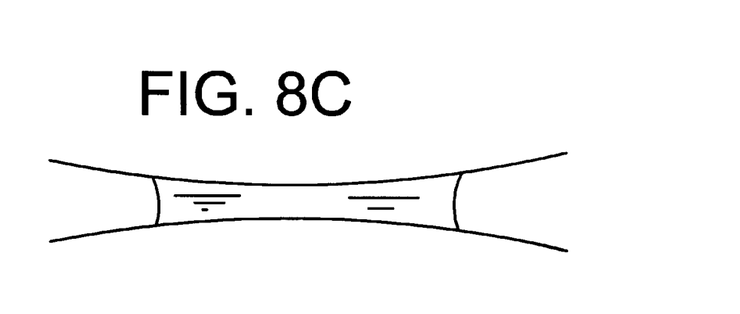
FIG. 8c is a schematic illustration of a capillary with throat.

4. Equilibrium in capillary with throat: Consider a capillary with a throat (FIG. 8c). If liquid is added to the throat region, equilibrium is achieved when the two wet/dry interfaces are the same diameter as shown.

Erythrocyte/plasma separation system hypothesis

It will be appreciated that the following analysis is merely to illustrate the general principles involved and is not device or material specific.

Figure 9A:
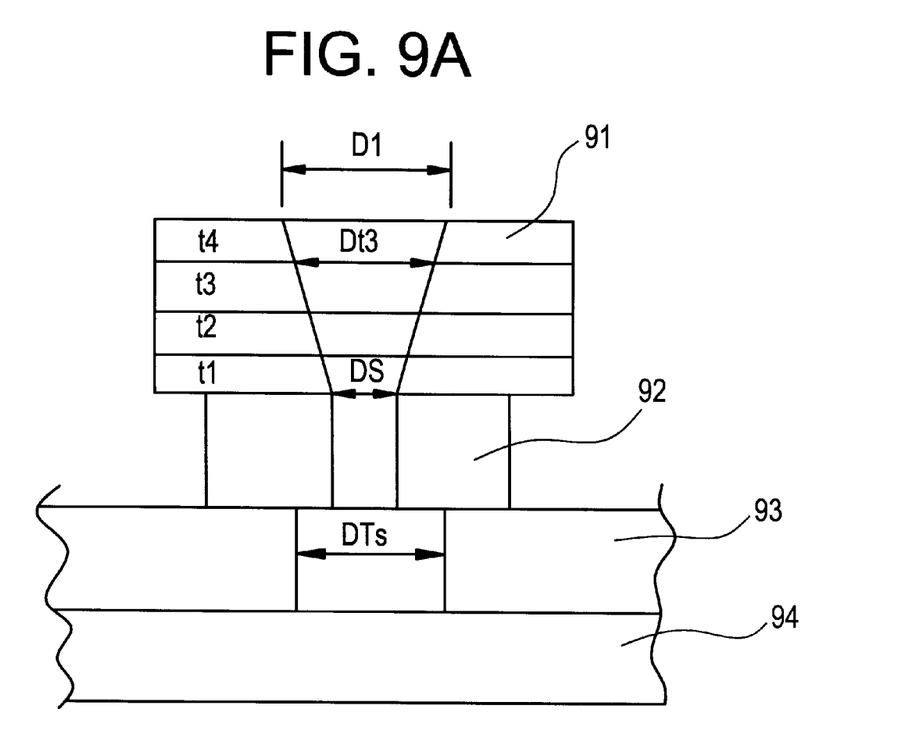
FIGS. 9a and 9b are schematic illustrations of separation system hypothesis.

Referring to FIG. 9a. In this example, the separation membrane 91 has an asymmetric pore structure, the larger pore size being adjacent the upper surface, and the smaller pores at the lower surface. The collection membrane 92 has a uniform pore structure and, in this example, the pores are the same size as the lower pores of membrane 91. This ensures that, providing the two membrane materials have the same surface chemistry, liquid will wick readily from the upper to lower membrane (see 2 above).

It will be appreciated that membrane 91 could have uniform pore structure, provided the pores were larger than that of membrane 92, and sufficiently large to allow passage of particulate matter being filtered. Similarly, uniform pore structure is not essential for membrane 92 providing it readily absorbs liquid from membrane 91.

The area of membrane 91 is arranged to have a filtering capacity in excess of that required for the test (see 1 above). The absorption volume of the membrane 92 substantially defines the plasma volume required for the test and, for a particular membrane, is defined by membrane area.

The lower membrane 93, has a larger pore size than membrane 92 so that initially wicking from membrane 92 into 93 is prevented (see 3 above). Membrane 93 coacts with test strip 94 which, in this example, would incorporate the reagents necessary for the test.

Figure 9B:
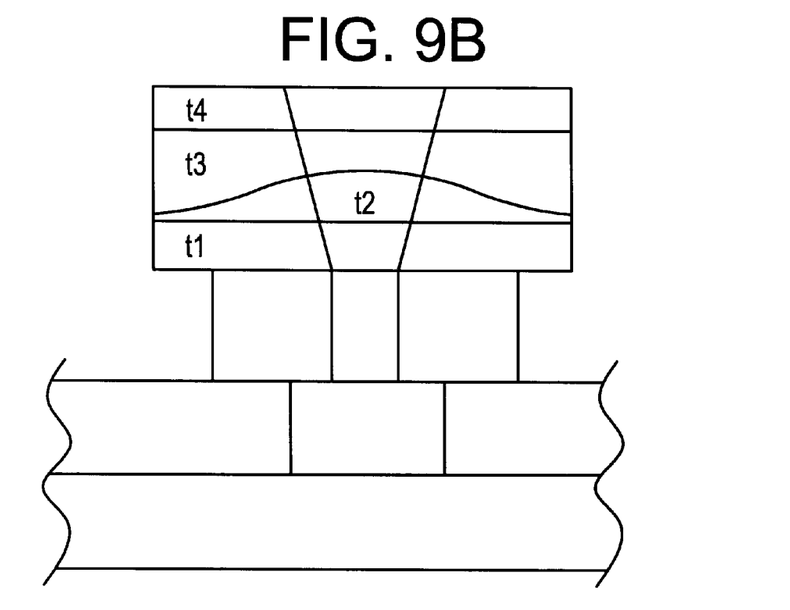

Superimposed on FIGS. 9a and 9b are diagrams of the pore size of the various porous materials:

D1 pore size of the upper surface of membrane 91

Dt3 pore size of the top of region t3

Ds pore size of the lower surface of membrane 91 and membrane 92

DTs pore size of the porous layer 93

It is emphasized that this is merely a representation of the pores and not a "literally" diagram. The pores are normally unidirectional and sponge-like in structure. The thickness of the membranes is shown greatly exaggerated.

In use, whole blood is applied to the upper surface of membrane 91. Pore size above region t1 allows passage of red cells but only plasma is allowed to flow into region t1 and into membrane 92. Plasma cannot flow into membrane 93 because of the larger pore size. The specific absorption volume of membrane 93 may be found by experiment and extrapolated for a particular volume or area required. The thickness of region t1 may be estimated from the pore size needed to filter out red cells and the upper and lower pore sizes of the membrane.

As whole blood is applied and plasma filtered, red cells build up in region t2. Region t3 contains any excess whole blood. Region t4 will be substantially free of liquid because of the capillarity of the underlying membranes.

If the pore size Dt3, corresponding to the top of region t3, exceeds the pore size DTs of membrane 93, plasma will flow into the latter and membrane 92 no longer defines the plasma volume (see 4 above). In other words, the system automatically controls plasma volume when there is sufficient plasma volume to fill membrane 92 and when dt3<DTs. Furthermore, if the maximum pore size of membrane 91 (at the upper surface) were smaller than DTs and excess blood flooded the upper surface, this would also cause loss of control.

It will be appreciated that for a given system, materials and dimensions, the thickness of regions t1, t2, t3 and t4 will depend on the volume of whole blood applied and the haematocrit thereof.

It is possible to mathematically model the relationship between the various parameters and compute their values. For example, the distribution of solids forming membrane 91 can be estimated knowing the extremes of pore size and distribution therein. Hence, the volume of liquid or erythrocytes occupying particular regions within the membrane can be computed using a series of simultaneous equations. These procedures will be apparent to those skilled in the art.

When whole blood has been applied and plasma has saturated membrane 92, the separation membrane 91 may be removed and discarded. Diluent is then applied to membrane 92, which since this is already saturated, causes plasma to be washed out into membrane 93 and hence into test strip 94 (see 3 above). Further diluent flow causes plasma to flow down the test strip followed by diluent.

Alternatively, removal of the separation membrane 91 may be avoided by applying diluent directly to membrane 92 in a region not covered by membrane 91.

It is emphasized that the aforementioned hypothesis assumes considerable simplification, and is intended merely as an aid to understanding the mechanism involved, and as a simplified design procedure. For example, it is assumed that the red cells form a region of uniform thickness t2 whereas, in practice, lateral flow causes non-uniform depositing of red cells as shown in FIGS. 1a 2, 3, 5d and 9b. The problem may be further complicated by lateral non-uniformity due to whole blood being applied at rectangular inlet regions.

Figure 6A:
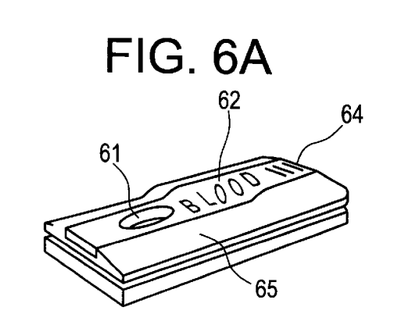
FIG. 6a is a perspective view of an interlocked device.

FIGS. 6a and b show a three dimensional view of interlocked device, and said device with filter removed respectively. This provides some degree of interlocking against misuse—such as omitting the diluent step. Interlocking was described in relation to FIGS. 4a to 4c. However, the principle may be incorporated into other devices described herein and elsewhere.

Figure 6B:
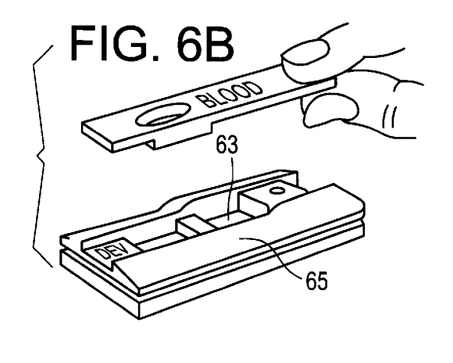
FIG. 6b is a perspective view of the interlocked device of FIG. 6a with the filter removed.

Filter assembly 61 incorporates opaque cover 62 which is located over test window aperture 63. Said cover also incorporates finger grip 64. Cover 62 may incorporate an operating instruction such as "BLOOD" to remind the operator to add blood to the filter funnel. Similarly the device housing 65 may incorporate operating instruction "DILUENT" to remind the operator to add diluent. This is only visible when filter assembly is removed. Hence, this provides interactive operating instruction, and some degree of inherent interlocking, in order to minimize operator error.

Plasma Collection Membrane: The preceding text was concerned mainly with maximizing the plasma available from filters. This section is concerned with storing the plasma in a collection membrane prior to use by the assay means, together with means of connecting the plasma to, and from, the collection membrane. It is not merely a case of increasing the surface area or thickness. Increasing the area may waste plasma due to stagnation entrapment caused by small inlet and outlet connection areas, and increasing the thickness may cause unacceptable plasma collection characteristics.

U.S. Pat. No. 5,240,862 describes the use of plasma "collection" membrane which is reputed to be inert and which appears to define the plasma volume. The following description relates particularly, but not exclusively, to the use of this material.

Figure 7A:
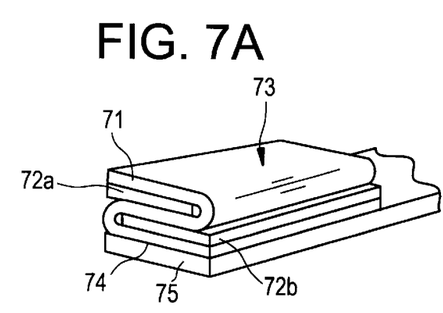
FIG. 7a is a perspective view of a Z-form collection device.

FIG. 7a shows a three dimensional view of a folded Z form of collection membrane 71 with convoluted and superimposed planes. Impervious membranes 72a and b serve to separate the folds of membrane 71. Outlet from plasma separation filter (not shown) is connected to inlet region 73, and outlet from collection membrane 74 is connected to assay device 75. The inlet and outlet regions each defining an end plane.

In use, whole blood is added to the plasma separation filter (as described previously), and plasma flows into collection membrane 71. Subsequently, the plasma separation filter is removed, and diluent added to region 73. This causes plasma within collection membrane to exit region 74 and flow into assay device 75. Hydrophobic mesh, or large pore porous media, may be interposed between outlet 74 and assay device, in order to prevent premature flow therein, prior to addition of diluent.

The construction allows use of a large collection membrane area, convenient connection to separation and assay devices, and avoids stagnation regions. Obviously, additional undulations may be used.. However, since the Primecare collection membrane is asymmetrical, an odd number of layers ensures that appropriate surfaces of said membrane connect with respective plasma and assay devices.

Figure 7B:
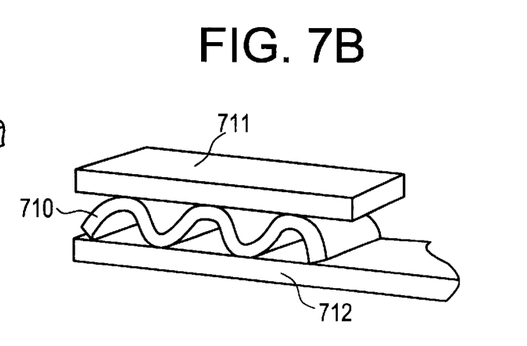
FIG. 7b is a perspective view of a W-form collection device.

FIG. 7b shows a three dimensional view of a wavelike W form collection device. This is also intended to provide increased plasma capacity. The peaks and troughs of plasma collection membrane 710 define end planes that contact outlet of separation device 711 and assay device 712, respectively.

The device operates, and is used, in much the same manner as the previous embodiment. A possible advantage is that, since the path length between inlet and outlet is shorter than FIGURES 71, both transfer of plasma to and from the device may be faster.

While the present invention has been described in connection with a specific embodiment thereof and in a specific use, various modifications will occur to those skilled in the art without departing from the spirit and scope of the invention as set forth in the appended claims. We therefore wish to embody within the scope of the patent which may be granted hereon all such embodiment as reasonably and properly come within the scope of my contribution to the art.

What is claimed is:

1. A filter device, for use in assay procedures, comprising a filter means having a first porous media having interconnected pores connected in laminate manner to a second porous media having interconnected pores, wherein at least a portion of said pores of said first porous media are substantially larger than said pores of said second porous media; an inlet region of said first porous media is arranged to receive liquid containing particulate matter to be filtered, and an outlet region of said second porous media connects the filtrate therefrom to an assay means; said first porous media allowing coplanar passage of at least part of said particulate matter; whereby said interconnected pores of second porous media trap and prevent passage of particulate matter, but allow coplanar passage of said filtrate; said liquid inlet region and said outlet region are arranged so that as said porous media becomes blocked with particulate matter; the liquid flow, and particulate matter contained therein, travel laterally, and then transversely, to unblocked regions of pores.

2. The device according to claim 1 wherein the inlet and outlet regions are laterally spaced, and the liquid flow therebetween, within the filter means, involves unidirectional flow in the lateral plane.

3. The device according to claim 1 wherein the inlet and outlet regions are in substantial opposing juxtaposition, and the liquid flow therebetween, within the filter means, involves contra-flow in the lateral plane.

4. The device according to claim 1 wherein the filter means is positioned symmetrically relative to the inlet and outlet, at least in one plane.

5. The device according to claim 1 wherein said second porous media provides filtrate collection means.

6. The device according to claim 5 in which said filtrate collection means substantially defines the volume of filtrate.

7. The device according to any one of claims 5 or 6 wherein said filter means incorporates a gradation of pore size, from large to small, through at least a portion of the thickness of said filter means.

8. The device according to any one of claims 1 or 5 in which first and second porous media are separable.

9. The device according to claim 8 wherein said filter means incorporates a gradation of pore size, from large to small, through at least a portion of the thickness of said filter means.

10. The device according to claim 9 wherein the assay means comprises a analytical strip, made from resilient material; portion of said strip is bent into a bowed form by deflection means; said filter support means is also made from resilient material, and deflected to conform to the said bowed form by bending means in order to bias filtrate outlet of filter device and assay means together in close contact.

11. The device according to claim 10 wherein said filter support means and bending means coact for easy application and removal of filter device from assay means.

12. The device according to claim 1 wherein the filter means includes a support means.

13. The device according to claim 12 wherein the support means defines at least the inlet region.

14. The device according to claim 12 wherein support means incorporates liquid retention means to retain said liquid, to be filtered, while filtering takes place.

15. The device according to claim 12 wherein the filter means is flat or curved in one or more planes.

16. The device according to claim 15 wherein the assay means comprises a analytical strip, made from resilient material; portion of said strip is bent into a bowed form by deflection means; said filter support means is also made from resilient material, and deflected to conform to the said bowed form by bending means in order to bias filtrate outlet of filter device and assay means together in close contact.

17. The device according to claim 16 wherein said filter support means and bending means coact for easy application and removal of filter device from assay means.

18. The device according to claim 12 wherein the filter device includes interlock means to ensure that said filter device is absent before result of said assay means can be ascertained.

19. The device according to claim 18 wherein said interlock means comprises an opaque cover, attached to said filter support means, which covers assay result means until said filter support is removed.

20. The device according to claim 19 wherein opaque interlock cover and assay means includes interactive operating instructions, in which certain words or phrases thereon inscribed are selectively uncovered.

21. The device according to claim 12 wherein the support means includes a filter attachment means, to at least to said first porous media.

22. The device according to claim 21, wherein filter attachment means is adhesive.

23. The device according to claim 22 wherein filter attachment means includes means for applying and removing said filter means from assay means.

24. The device according to claim 23 wherein support means includes means of applying controlled bias force between said outlet of filter means and aid assay means.

25. The device according to any one of claims 1, 5 or 6, 2, 3, 4, 13, 21, 22, 23 or 24 wherein the filter means is flat or curved in one or more planes.

26. The device according to claim 1 additionally comprising porous material in the form of a prefilter or spreading layer which coacts with said first porous media to provide additional filtering capacity.

27. The device according to claim 26 wherein said porous media is made from glass fiber.

28. The device according to claim 1 wherein assay means includes filtrate collection means, or additional filtrate collection means.

29. The device according to claim 28 wherein filtrate collection means comprises porous media.

30. The device according to claim 29 wherein said porous media comprises a polymeric membrane.

31. The device according to claim 30 wherein the surface to surface pore distribution of the polymeric membrane is asymmetrical.

32. The device according to claim 29 wherein characteristics and dimensions of said collection membrane substantially define volume of filtrate.

33. The device according to claims 1, 5 or 6, 2, 3, 4, 13, 21, 22, 23, 24, 18, 19, 20, 14, 26, 27, 28, 29, 30, 31 or 32 wherein the assay means comprises a analytical strip, made from resilient material; portion of said strip is bent into a bowed form by deflection means; said filter support means is also made from resilient material, and deflected to conform to the said bowed form by bending means in order to bias filtrate outlet of filter device and assay means together in close contact.

34. The device according to claim 33 wherein said filter support means and bending means coact for easy application and removal of filter device from assay means.

35. The device according to any one of claims 1, 5 or 6, 2, 3, 4, 13, 21, 22, 23, 24, 18, 19, 20, 14, 26, 27, 28, 29, 30, 31 or 32 wherein any porous media or combination thereof, is bent into a convoluted superimposed or wavelike form.

36. The device according to claim 35 wherein the folded convoluted superimposed or wavelike forms are defined by end planes at least said end planes defining liquid inlet and outlet regions.

37. The device according to claim 35 wherein the folded convoluted superimposed or wavelike forms are defined by end planes, at least said end planes connected to liquid inlet and outlet regions.

38. The device according to claim 35 wherein the assay means comprises a analytical strip, made from resilient material; portion of said strip is bent into a bowed form by deflection means; said filter support means is also made from resilient material, and deflected to conform to the said bowed form by bending means in order to bias filtrate outlet of filter device and assay means together in close contact.

39. The device according to claim 38 wherein said filter support means and bending means coact for easy application and removal of filter device from assay means.

* * * * *